(12) United States Patent
Mahvi et al.

(10) Patent No.: US 8,777,938 B2
(45) Date of Patent: Jul. 15, 2014

(54) FAN-BEAM MICROWAVE HORN FOR BLOODLESS RESECTION

(75) Inventors: David M. Mahvi, Middleton, WI (US);
Mark C. Converse, Madison, WI (US);
Punit Prakash, San Francisco, CA (US);
John G. Webster, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 996 days.

(21) Appl. No.: 12/478,525

(22) Filed: Jun. 4, 2009

(65) Prior Publication Data

US 2010/0312234 A1 Dec. 9, 2010

(51) Int. Cl.
*A61B 18/04* (2006.01)
(52) U.S. Cl.
USPC .............................. 606/33; 607/156; 607/101
(58) Field of Classification Search
USPC ...................................... 606/33; 607/154, 156
See application file for complete search history.

(56) References Cited

U.S. PATENT DOCUMENTS

| | | | |
|---|---|---|---|
| 6,104,959 A * | 8/2000 | Spertell | 607/101 |
| 2001/0029368 A1* | 10/2001 | Berube | 606/33 |
| 2002/0128642 A1* | 9/2002 | Berube et al. | 606/33 |
| 2003/0125720 A1* | 7/2003 | Woodard et al. | 606/15 |
| 2005/0062664 A1* | 3/2005 | Hidai et al. | 343/786 |
| 2006/0064084 A1* | 3/2006 | Haemmerich et al. | 606/41 |
| 2006/0089637 A1* | 4/2006 | Werneth et al. | 606/41 |
| 2006/0135962 A1* | 6/2006 | Kick et al. | 606/108 |
| 2008/0045938 A1* | 2/2008 | van der Weide et al. | 606/33 |
| 2008/0269851 A1* | 10/2008 | Deem et al. | 607/101 |

FOREIGN PATENT DOCUMENTS

WO WO2006/077567 7/2006
WO WO2006/127847 11/2006

* cited by examiner

*Primary Examiner* — Jaymi Della
(74) *Attorney, Agent, or Firm* — Boyle Fredrickson, S.C.

(57) ABSTRACT

A method of resection of an organ employs a handheld microwave waveguide that receives a microwave signal and applies a substantially planar microwave beam into the organ for coagulation of a strip of tissue in an organ providing a barrier against blood loss during resection operations.

13 Claims, 3 Drawing Sheets

FAN-BEAM MICROWAVE HORN FOR BLOODLESS RESECTION

STATEMENT REGARDING FEDERALLY SPONSORED RESEARCH OR DEVELOPMENT

This invention was made with United States government support awarded by the following agency:
NIH DK058839
The United States government has certain rights in this invention.

CROSS-REFERENCE TO RELATED APPLICATIONS

--

BACKGROUND OF THE INVENTION

The present invention relates to surgical resection of tissue and in particular to an apparatus using microwave coagulation to control bleeding during the resection of a portion of an organ.

The liver is a common site for both primary and metastatic cancer. Surgical resection (hepatectomy) is currently the preferred treatment for liver cancer. During resection, the surgeon typically removes a lobe of the liver, a time consuming procedure where the surgeon must cut through tissue while avoiding or closing large blood vessels. Blood loss during this procedure can adversely affect patient survival, increase hospital stay, and increase complication rates.

Some studies have investigated the use of radio frequency (RF) ablation or microwave (MW) ablation to coagulate tissue before resection. In RF ablation, one or more electrodes are inserted into the tissue and current passing from the electrodes through the patient to a large area ground pad on the patient's skin coagulates the tissue near the electrode through resistive heating, sealing it against blood flow. In order to ablate the necessary area of tissue, the electrode is removed and reapplied at a series of locations along the tissue slice. The time required for this procedure is generally too long for clinical practice.

Pending US patent application 2006/0064084 published Mar. 13, 2006 and entitled: "Electrode Array for Tissue Ablation" describes a system for RF ablation using multiple electrodes positioned within a holder for insertion into the tissue along an ablation line. The use of multiple electrodes greatly reduces the time required for this procedure.

SUMMARY OF THE INVENTION

The present invention provides a microwave horn antenna that may be used in lieu of insertable electrodes for creating a coagulated zone for bloodless resection. The horn antenna is compact for easy manipulation by a surgeon and produces a fan-shaped microwave radiation pattern leading to heating in a region conforming to a resection plane and minimizing the generation of high temperature water vapor such as makes the coagulation process less controllable. A dielectric within the horn allows the use of lower frequencies which propagate more deeply into the tissue. A quarter wavelength stub provides improved shaping of the emission pattern and an insulating coating allows handheld operation with inevitable heating of the horn at the necessary power.

Specifically, the present invention provides a method for bloodless resection of an organ by applying microwave energy along a resection line through a microwave horn antenna emitting a generally fan-shaped microwave beam having an elongated cross-section whose longest dimension is aligned with the resection line. After the resection line is coagulated, a cut is made along the resection line within the coagulated tissue to resect the organ.

It is thus one object of the invention to provide a rapid method of coagulating a zone within an organ for bloodless resection without the need for the placement of electrode arrays.

The coagulation and cutting steps may be repeated to continue resection of the organ at an increasing depth along a plane aligned with the resection line.

It is thus an object of the invention to provide a method that accommodates limited microwave penetration and that provides a flexible and incremental procedure that accommodates variances and uncertainty in tissue depth.

The longest cross-sectional dimension of the microwave horn may be more than twice the height of the cross-section perpendicular to the longest dimension.

It is thus an object of the invention to provide a microwave emission pattern that reduces internal heat concentrations in the tissue such as generate migrating high temperature water vapor.

The microwave horn may be filled with a solid dielectric material such as Macor® and the microwave energy may be substantially at a frequency of less than 4 GHz.

It is thus an object of the invention to permit the microwave horn to be used with lower frequency microwave energy for greater penetration while maintaining a compact size that may be inserted between partially resected tissue walls for movement along the resection line by the surgeon.

The horn is sized to be held within a surgeon's hand and has an outer surface tactility indicating the orientation of the longest dimension and the direction of microwave emission.

It is thus an object of the invention to provide a system amenable to use by a single individual who may wield both the microwave horn and a scalpel.

The method may move the microwave horn along the resection line and apply sequential microwave applications over a distance larger than the longest dimension.

It is thus an object of the invention to provide a system that can work for arbitrary organ sizes while maintaining a compact form factor.

The microwave horn may include a flexible coaxial cable removably connected to the horn to provide microwave power thereto in an amount greater than 50 W.

It is thus an object of the invention to provide a high power microwave device that allows relatively quick coagulation of tissue.

The dielectric of the microwave horn may further include metal inserts within the dielectric for field shaping.

It is thus an object of the invention to permit cross-sections of high aspect ratio enabling faster coagulation of longer sections.

The horn may have its outer surfaces covered by a thermally insulating coating.

It is thus an object of the invention to manage transmission inefficiencies while preserving handheld operation.

These particular objects and advantages may apply to only some embodiments falling within the claims and thus do not define the scope of the invention.

DETAILED DESCRIPTION OF THE PREFERRED EMBODIMENT

Figure 1:
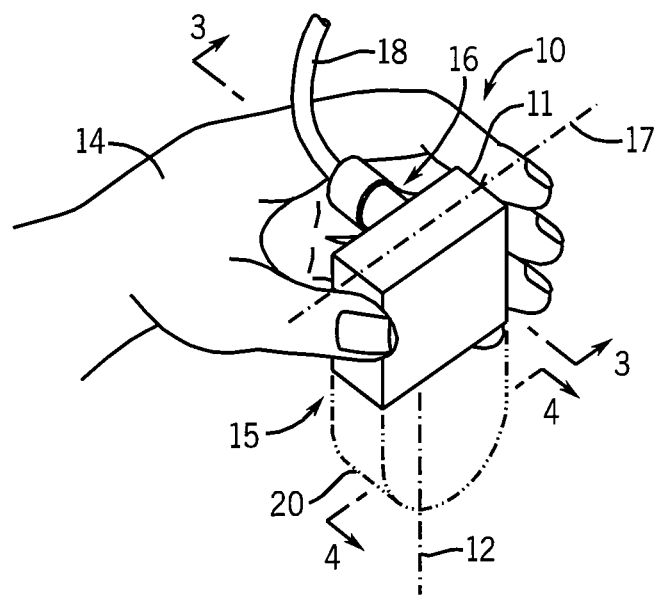
FIG. 1 is a perspective view of the microwave device of the present invention as can be held in one hand showing generally a coagulation region from microwaves projected downward along an axis.

Referring now to FIG. 1, a microwave applicator 10, in a first embodiment of the present invention, provides a generally rectangular housing 11 having outer dimensions of approximately 4×4.5×2 cm. As depicted in FIG. 1, and in use, the longest dimension is oriented vertically and aligns with a microwave propagation axis 12 extending downward from a lower face 15 of the microwave applicator 10. The width of 4 cm is along the housing's transverse axis 17 allowing it to be comfortably grasped in a surgeon's hand 14 between the thumb and fingers thereby to be readily manipulated in orientation.

A standard N-type flanged microwave connector 16 is attached to a rear vertical wall of the housing 11 to releaseably connect the microwave applicator 10 to a flexible coaxial microwave cable 18. This attachment allows the cable 18 to pass over the hand 14 and be supported and guided thereby. The outer dimensions of the housing 11 of the microwave applicator 10 and its orthogonal walls provide tactile feedback indicating the orientation of the housing 11.

A generally fan shaped microwave beam is emitted from the microwave applicator 10 providing a coagulation region 20 approximately 1.8 cm long in a direction aligned with the transverse axis 17 and approximately 1.1 cm in depth along the axis 12, when the microwave applicator 10 is placed with its lower face 15 against tissue.

Figure 2A:
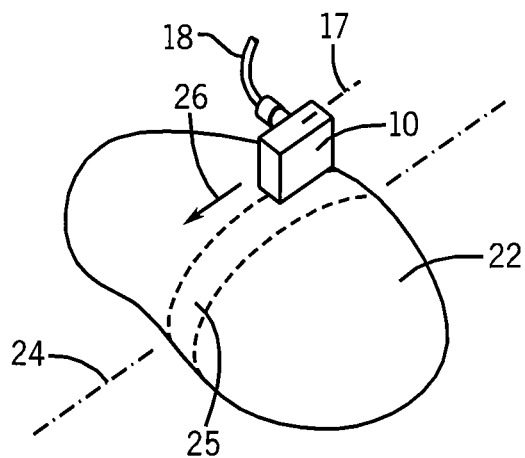
FIGS. 2a-2c are perspective views of the device of FIG. 1 being used to resect an organ through successive coagulation and cutting operations.

Referring now to FIG. 2a, the microwave applicator 10 may be placed with its lower face 15 against an upper surface of an organ 22 that will have a portion resected. The transverse axis 17 of the microwave applicator 10 is oriented to be parallel to the resection line 24 and the microwave applicator 10 is moved transversely, as indicated by arrow 26, to successive locations along the resection line 24 while following the upper surface of the organ 22. At each successive location, microwave power of up to 90 W may be applied for approximately 30 seconds to provide a set of rectangular coagulation zones together forming a continuous coagulation strip 25 along the resection line 24.

Figure 2B:
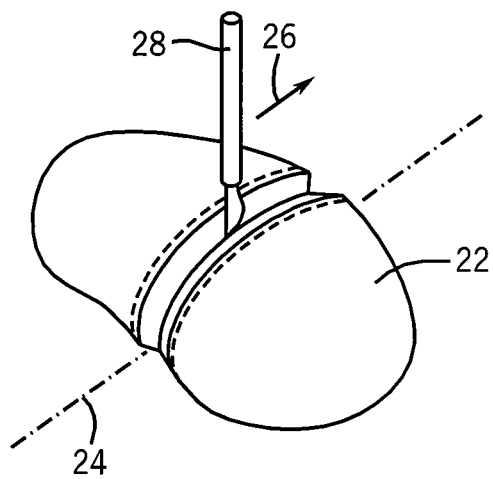

Referring to FIG. 2b, the coagulation strip 25 may then be resected using a scalpel 28, again moving transversely as indicated by arrow 26 cutting through the coagulation strip to prevent bleeding. Generally, this cut may not completely sever the organ 22, such as the liver, whose thickness exceeds the limited depth of the coagulation region 20.

Figure 2C:
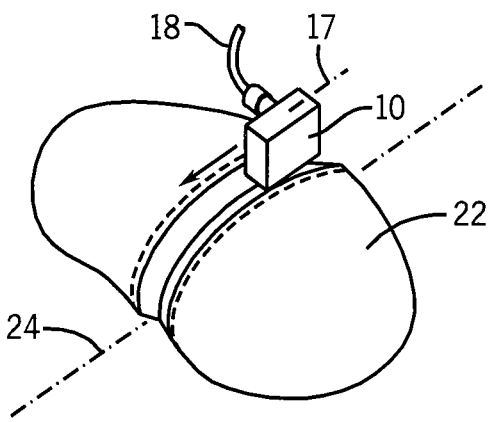

In this case, and referring to FIG. 2c, the microwave applicator 10 may be inserted into the cut made by the scalpel 28 and the process of coagulation per FIG. 2a above repeated with the lower face 15 of the microwave applicator 10 adjacent to tissue in the bottom of the cut. Successive coagulation and cutting permits organs of irregular dimensions to be readily resected by multiple passes of the microwave applicator 10, possibly changing the transverse distance moved by the microwave applicator 10 at the various levels through the organ 22 as the transverse width of the organ 22 changes with depth. The present inventors recognize that this process may be repeated for an arbitrary number of times of successive cutting and coagulation per FIGS. 2b and 2c to handle organs thicker than the depth of the coagulation region 20 available from the microwave applicator 10 provided the microwave applicator 10 were compact and manipulable.

Figure 3:
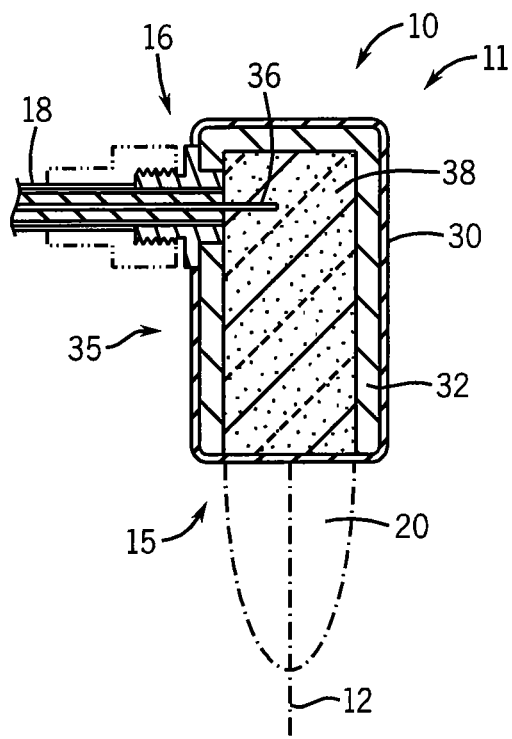
FIG. 3 is a side elevational cross-section of the device of FIG. 1 taken along lines 3-3 showing an internal dielectric material and coupling of microwave power to the dielectric material by means of a quarter wavelength stub.

Referring now to FIG. 3, the outer surface of the housing 11 may present a layer of electrically and thermally insulating material 30, for example, epoxy covering an inner conductive metallic shell 32. The metallic shell forms walls of a rectangular box opened at the lower face 15 and thereby defines a generally rectangular inner volume contained between the walls of the conductive metallic shell 32. A rear wall 35 of the metallic shell 32 and its insulating material 30 may be pierced by the microwave connector 16 at its upper end to permit the introduction of a quarter wavelength stub 36 conductor from the co-axial cable 18 into the inner volume.

The stub 36 may be received within a solid dielectric material 38 filling the inner volume, the dielectric material preferably being Macor®, a machinable glass ceramic material available from Corning Inc. having offices worldwide. Macor® generally provides a dielectric constant greater than 5.5, a dielectric strength of approximately 9.4 kV/mm and a coefficient of expansion of approximately $93 \times 10^{-7}/°C$.

The metallic shell 32 connects electrically to the outer conductor of the waveguide formed by the microwave coaxial cable 18 and together with the quarter wavelength stub 36, creates a tuned cavity controlling the coagulation region 20. The solid dielectric material 38 permits the waveguide to operate at the lower frequency microwaves of 2.45 GHz while retaining a compact handheld form factor.

Figure 4:
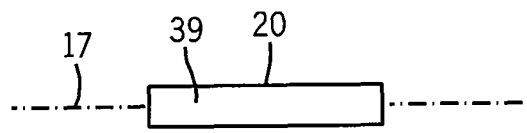
FIG. 4 is a cross-section taken along lines 4-4 of a rectangular microwave pattern that reduces high center temperatures.
Figure 5:
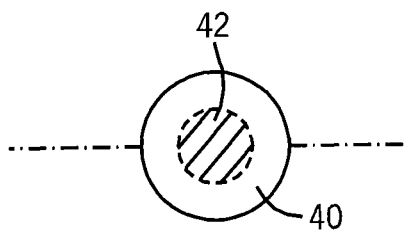
FIG. 5 is a figure similar to that of FIG. 4 showing the emission cross-section of a typical microwave cylindrical horn such as produces high center temperatures causing migration of high temperature water vapor disrupting the coagulation pattern.

Referring now to FIGS. 4 and 5, generally the coagulation region 20 has an aspect ratio (the ratio of a dimension along the transverse axis 17 to a dimension perpendicular to the transverse axis 17 in a cross-sectional plane perpendicular to the radiation axis 12) of greater than one to promote coagulation in a thin strip of tissue 39 of the greatest possible length for a given power. In the first embodiment, a coagulation region having cross-sectional dimensions of 3×2.5 cm and an aspect ratio of 1.2 is obtained. A high aspect ratio as provided by the present invention provides an improved, relatively uniform heating within the coagulation region 20. In contrast a generally circular coagulation region 40 provided by standard microwave horns promote the development of an over-temperature region 42 resulting from the relatively thick layer of elevated temperature of the surrounding tissue preventing the escape of heat. It is believed that such over-temperature regions 43 create high temperature water vapor that migrates through the tissue changing the coagulation region unpredictably.

Figure 6:
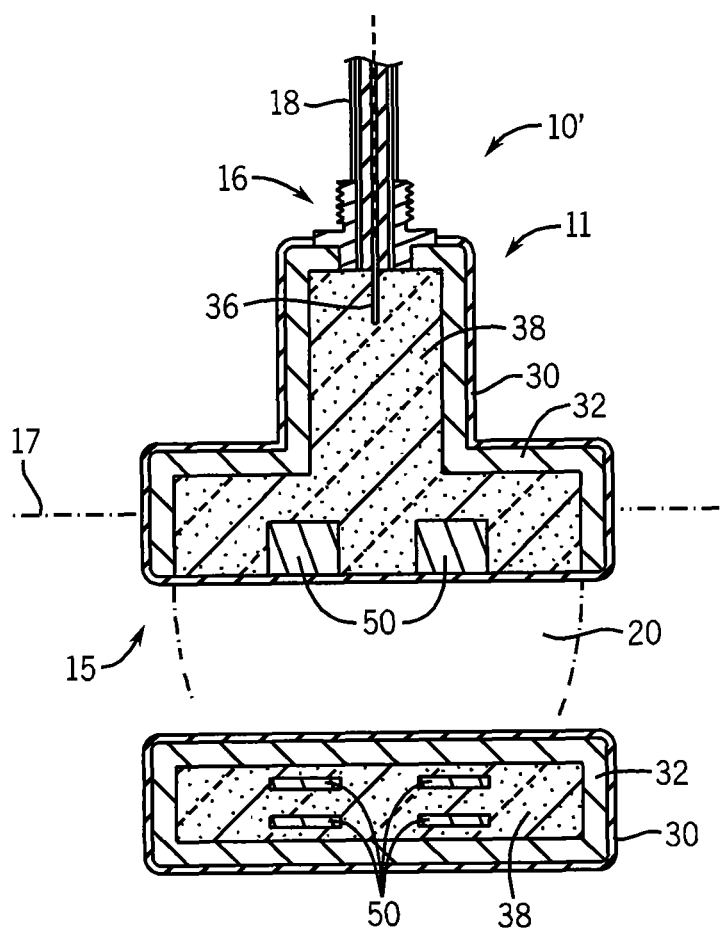
FIG. 6 is a front elevational cross-section and bottom plan view of an alternative embodiment of the FIG. 1 having metal inserts increasing the aspect ratio of the microwave cross-section.

Referring now to FIG. 6, an alternative embodiment of the applicator 10' can provide even a higher aspect ratio in the cross-section of the coagulation region 20 by using metallic shell 32 having an internal volume with an inverted T-shaped elevational cross-section so that the lower face 15 of the housing 11 flares along the transverse axis 17. Metallic inserts 50 placed within the dielectric material 38 at the lower face 15 provide field shaping to extend the coagulation region 20 into this higher aspect ratio. Simulations of this design have indicated that a cross-section of the coagulation region 20 having dimensions of approximately 5.5×1.75 cm and thus an aspect ratio of greater than 3 may be obtained to produce a coagulation region 20 with a tissue depth of 1.25 cm.

It is specifically intended that the present invention not be limited to the embodiments and illustrations contained herein, but include modified forms of those embodiments including portions of the embodiments and combinations of elements of different embodiments as come within the scope of the following claims.

We claim:

1. A method for resection of an organ comprising the steps of:
   (a) applying microwave energy along a resection line through the use of a microwave horn antenna, the microwave horn antenna projecting, into the organ, a generally fan-shaped microwave beam having an elongated cross-section along a plane perpendicular to a propagation direction of the microwave beam, the cross section having a dimension along a transverse axis within the plane substantially larger than a dimension within the plane perpendicular to the transverse axis, wherein a longest dimension of the cross-section is aligned with the resection line to coagulate tissue along the resection line and so that the microwave horn antenna remains apart from the coagulated tissue; and
   (b) cutting along the resection line within the coagulated tissue to resect a portion of the organ.

2. The method of claim 1 further including the step of:
   (c) repeating steps (a) and (b) to continue resection of the organ at an increasing depth along a plane aligned with the resection line.

3. The method of claim 1 wherein the longest dimension is more than a dimension of the cross-section perpendicular to the longest dimension.

4. The method of claim 1 wherein the microwave horn is filled with a solid dielectric material.

5. The method of claim 4 wherein the solid dielectric material is a ceramic.

6. The method of claim 4 wherein the microwave energy is substantially at a frequency of less than 4 GHz.

7. The method of claim 6 wherein the microwave horn antenna is sized to be held within a surgeon's hand and has an outer surface tactility indicating a rotational orientation of the microwave horn antenna about an axis of microwave emission and the direction of microwave emission.

8. The method of claim 1 wherein step (a) includes the step of moving the microwave horn antenna along the resection line and applying microwaves over a distance larger than the longest dimension.

9. The method of claim 1 wherein the organ is a liver.

10. The method of claim 1 wherein the microwave horn antenna transmits at least 50 W of power to the tissue.

11. The method of claim 1 wherein the cross-section is substantially 5.5×1.75 cm.

12. The method of claim 1 wherein the longest dimension of the cross-section is no less than two times a dimension of the cross-section perpendicular to the longest dimension, the microwave horn antenna having an outer surface size to be held by a surgeon in one hand to be freely moved in angle and translation, the outer surface providing tactile features indicating orientation of an axis of the microwave horn antenna in rotation, the microwave horn antenna comprising an outer rectangular metallic shell with an internal dielectric material for operation at less than four gigahertz.

13. The method of claim 12 wherein a quarter wavelength stub is used at the edges of the microwave horn antenna to constrain the radiation pattern and improve uniformity of radiation depth penetration.

* * * * *